United States Patent [19]

Buzas et al.

[11] 4,382,935
[45] May 10, 1983

[54] ANALGESIC DRUG CONTAINING A DERIVATIVE OF BENZYLPIPERAZINE

[75] Inventors: André Buzas, 25 route de Versailles, 91570 Bievres; Jean-Marie Melon, 158 rue de Courcelles, 75017 Paris, both of France; Gilbert Lavielle, Orleans; André Champagnac, Bresles, both of France

[73] Assignees: André Buzas, Bievres; Jean-Marie Melon, Paris; Laboratoires Sauba S.A., Montreuil; Universite d'Orleans, Orleans, all of France

[21] Appl. No.: 229,532

[22] Filed: Jan. 29, 1981

[30] Foreign Application Priority Data

Feb. 14, 1980 [FR] France ................................ 80 03284

[51] Int. Cl.³ .................. A61K 31/495; C07D 405/04
[52] U.S. Cl. .................................... 424/250; 544/373; 544/376
[58] Field of Search .......................... 424/250; 544/376

[56] References Cited

U.S. PATENT DOCUMENTS 3,156,688 11/1964 Zaugg et al. ...................... 544/376
3,459,830 8/1969 Huebner et al. ................... 544/376
3,496,186 2/1970 Descamps et al. ................ 544/376
4,221,793 9/1980 Weber et al. ...................... 544/376
4,276,294 6/1981 Bowman ........................... 544/376

FOREIGN PATENT DOCUMENTS 2421990 2/1979 France .
1570374 2/1981 United Kingdom .

OTHER PUBLICATIONS

Journal of Organic Chemistry, vol. 38, No. 9, May 4, 1979.

Primary Examiner—Donald G. Daus
Assistant Examiner—James H. Turnipseed
Attorney, Agent, or Firm—Young & Thompson

[57] ABSTRACT

The drug contains an active substance consisting of 1-(3'-benzofuryl)-4-benzylpiperazine. In order to prepare the compound, a reaction is carried out with reflux between 3-coumaranone and N-benzylpiperazine in the presence of acetic acid and in an aromatic solvent.

2 Claims, No Drawings

ANALGESIC DRUG CONTAINING A DERIVATIVE OF BENZYLPIPERAZINE

This invention relates to an analgesic drug containing a derivative of benzylpiperazine as active substance.

A very large number of analgesic drugs are already known.

French patent Application No. 2,421,900 filed on Mar. 17th, 1977 in the name of the present Applicants described piperazino-3-indoles which are endowed with analgesic properties and correspond to the following general formula:

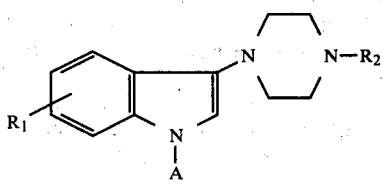

wherein:
A is a hydrogen atom, a carboxylic acid radical or a substituted or unsubstituted alkyl, alkylaminoalkyl, benzyl or phenyl group,
$R_1$ is a hydrogen atom or chlorine atom or a lower alkyl, methoxy or hydroxy group,
$R_2$ is an alkyl, benzyl or phenyl group or a substituted or unsubstituted cyclic or heterocyclic group.

Among these compounds, the most active is 1-acetyl-3-benzylpiperazino-indole. This compound has remarkable analgesic properties which are comparable with those of morphine.

In accordance with this invention, the present Applicants have discovered a novel drug containing a derivative of benzylpiperazine as active substance; the analgesic properties of this drug are superior to those of the known compound mentioned above and to those of morphine without being attended by the known disadvantages of this latter.

In accordance with the invention, this analgesic drug essentially contains 1-(3'-benzofuryl)-4-benzylpiperazine as active substance.

This compound has the following developed formula:

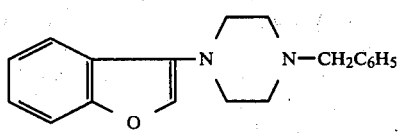

This compound is provided in the pure state in the form of crystals having a melting point of 120° C.

The empirical formula of the compound in accordance with the invention is written: $C_{19}H_{18}N_2O$. Elementary analysis of this compound has produced the following results:

|  | C | H | N |
|---|---|---|---|
| % theoretical: | 78.05 | 6.90 | 9 58 |
| % found: | 78.28 | 6.87 | 9.59 |

In nuclear magnetic resonance (NMR) in $CDCl_3$, the following results are obtained:

7.6–7.0 (10H, m,

$C_6H_5$, O—C$\underline{H}$=C);
3.5 (2H, s, C$\underline{H}_2$-C$_6$H$_5$); 3.2–2.9 (4H, m) and 2.8–2.5 (4H, m), 4N—C$\underline{H}_2$).

In thin-layer chromatography, the following results are obtained:
Rf=0.50 (20% ether in methylene chloride)
Rf=0.75 (10% methanol in methylene chloride).

In order to prepare 1-(3'-benzofuryl)-4-benzylpiperazine, the procedure is as follows: a reaction is conducted with reflux between 3-coumaranone and N-benzylpiperazine in the presence of acetic acid and in an aromatic solvent.

Preferably, the quantity of N-benzylpiperazine employed is slightly in excess with respect to the stoichiometric quantity which is theoretically necessary.

A detailed procedure for the preparation of the compound will be given hereinafter by way of numerical example and not in any limiting sense.

A quantity of 8 g (0.06 mole) of 3-coumaranone, 12.6 g (0.072 mole) of N-benzylpiperazine and 1.2 ml of acetic acid are mixed together in 180 ml of dry toluene.

The above mixture is refluxed with agitation within a reaction vessel equipped with a Dean-Stark separator for a period of eight hours. Approximately 1 ml of water is thus entrained. The greater part of the solvent (toluene) is evaporated in vacuum. The residue thus obtained is washed several times with water by trituration and then dissolved in 100 ml of boiling ethyl alcohol.

After cooling, the precipitate is dewatered, again washed with ethyl alcohol and the product is recrystallized in 200 ml of isopropanol in the presence of animal black.

After filtration, the product is washed with a small volume of isopropanol and the solid product is dried in vacuum at 40° C. There are thus obtained 8.5 g of product in accordance with the invention, namely with a yield of 48% with respect to the starting product.

The pharmaceutical properties of the compound in accordance with the invention will now be set forth. These properties are compared hereinafter with 1-acetyl-3-benzylpiperazine-indole which is described in French patent Application No. 2,421,900 filed on Mar. 17th, 1977 in the name of the present Applicants.

Acute toxicity in mice (DL50)

The acute toxicity is evaluated according to the mortality observed during a period of 48 hours on batches of four mice which have received perorally 100, 200, 400, 800 and 1600 mg/kg of the compound under study. The following results are thus obtained:
Known compound:
DL50=3000 micro-moles per kg (1000 mg/kg)
Compound in accordance with the invention:
DL50=5500 micro-moles per kg (1600 mg/kg).

The acute toxicity of the compound in accordance with the invention is consequently lower than that of the known derivative.

Analgesic activity

Siegmund test with phenylbenzoquinone in mice:

This test has been performed in accordance with the method described by Siegmund, Cadmus and Lu ("A method for evaluating both non-narcotic and narcotic analgesics", Proc. Soc. Exp. Biol. Med., 1957, 95, 729–731).

One hour after peroral administration of the product under study to batches of twelve mice per dose, phenylbenzoquinone in solution in a proportion of 0.02% in water containing 5% ethyl alcohol is administered by intraperitoneal injection in a proportion of 0.25 ml per mouse of 20 g.

The contortions displayed by each animal between the fifth and the tenth minute following injection of phenylbenzoquinone are then counted.

The dose DE50 (which produces a 50% reduction in the number of contortions with respect to the reference animals) is calculated on the basis of the dose/effect relation. The following results are thus obtained:

Known compound:
DE50 = 55 micro-moles per kg (18 mg/kg)
Derivative in accordance with the invention:
DE50 = 22 micro-moles per kg (6.5 mg/kg).

The results of this test therefore show that the product in accordance with the invention is more efficacious.

Heating-plate test performed on mice (Eddy test)

This test has been carried out in accordance with the method described by N. B. Eddy (J. Pharmacol. 1932, 45, 339–359).

One hour after the product under study has been administered perorally to batches of twelve mice per dose, the time taken by the mice to lick their front paws is measured, the mice having been placed on a plate heated to a temperature of 56.5° C.

The dose DE30 (which produces a 30% increase in licking time with respect to the reference animals) is calculated on the basis of the dose/effect relation.

The following results are thus obtained:

Known derivative:
DE30 = 40 micro-moles per kg (13 mg/kg)
Derivative in accordance with the invention:
70 micro-moles per kg (20 mg/kg)

Antagonism produced by Naloxone

This antagonism is sought in the Siegmund test performed on mice with phenylbenzoquinone as described earlier. Naloxone is administered by subcutaneous injection at a fixed dose at the same time as the product under study. The following results are thus obtained:

in the case of the known compound (in the presence of 16 micro-moles per kg of Naloxone):
DE50 = 45 micro-moles per kg (15 mg/kg)
in the case of the derivative in accordance with the invention (in the presence of 8 micro-moles per kg of Naloxone):
DE50 = 46 micro-moles per kg (13.5 mg/kg).

Interactions in vitro

Action on isolated organs.

These interactions are sought on isolated organs which are maintained in a state of survival in a nutrient liquid. The contractions of these organs are recorded on a kymograph by means of an isotonic mechanism.

An agonist is added to the nutrient liquid bath, either alone or after addition of an antagonist, to increasing concentrations which serve to plot cumulative dose-response curves.

The affinity parameter of an agonist (pDx), the competitive or non-competitive nature of an antagonism and the affinity parameter of a competitive antagonist (pAx) are estimated on the basis of a qualitative and quantitative study of the families of dose/response curves.

Antagonism with respect to histamine

In this test, the organ on which this action has been studied is the guinea-pig ileum. The nutrient liquid employed is Tyorode, the agonist is histamine and the antagonist is the product under study.

The following results have thus been obtained:
in the case of the known product: non-competitive antagonist;
in the case of the product in accordance with the invention: competitive antagonist, the affinity parameter ($pA_2$) having been found equal to 5.99.

Antagonism with respect to serotonin

The organ under study is the rat fundus, the nutrient liquid employed is Kreps liquid, the agonist is serotonin and the antagonist is the product under study.

The following results have thus been obtained:
in the case of the known compound: competitive antagonist, ($pA_2 = 5.34$);
in the case of the derivative in accordance with the invention: non-competitive antagonist.

Agonism on the rat fundus

The organ under study is the rat fundus, the nutrient liquid is the Kreps liquid and the agonist is the product under study.

The following results have been obtained:
in the case of the known derivative: affinity parameter ($pD_2 = 5.4$);
in the case of the derivative in accordance with the invention: affinity parameter ($pD_2 = 7.0$).

Antagonism produced by harmine

The organ studied in this case is the rat fundus the nutrient liquid is the Kreps liquid, the agonist corresponds to the product under study and the antagonist is harmine.

The following results have thus been found: with respect to the known product, harmine has a non-competitive antagonism; with respect to the product in accordance with the invention, harmine exhibits a competitive antagonism and the affinity parameter ($pA_2$) has been found equal to 6.85.

Fixation on morphine-compound cerebral receptors

It is sought to determine the affinity of the products under study by means of their capacity for displacement of tritiated etorphin in a rat-brain homogenate (containing 1 mg/ml of protein) over a period of 30 minutes at 35° C. This test consists in determining the value CI50 corresponding to the concentration of products which are capable of inhibiting 50% of the specific radioactive ligand bond.

The following results have thus been found:
known product: 103,000 nmol/l;
product in accordance with the invention: higher than 300,000 nmol/l.

By way of comparison, the morphine concentration CI50 is 179 nmol/l.

The results of the aforementioned pharmacological tests show that the product in accordance with the invention is a compound which, especially by virtue of its action in the Eddy test, exhibits central analgesic properties such as those defined in the article by D. R. Laurence and A. L. Bacharach (Evaluation of Drug Activities: Pharmacometrics, Academic Press, London and New York, 1964). However, it is not possible to demonstrate any relationship with the morphine compound receptors. The general properties of the compound in accordance with the invention are comparable with those of the known product employed in the tests mentioned in the foregoing but it is worthy of note that the analgesic properties of the product in accordance with the invention are appreciably superior. A surprising and unexpected finding, however, is the fact that the two compounds show a fundamental difference in regard to their action at the molecular level. This is wholly evidenced by their radically opposite activities in the tests relating to antagonism produced by Naloxone and to interactions in vitro on isolated organs. In fact, in accordance with the results of tests involving antagonism by Naloxone, the product in accordance with the invention is antagonized by Naloxone whereas the known compound is not antagonized. Similarly, in the test involving interactions in vitro on isolated organs, the compound in accordance with the invention is a competitive antagonist with respect to histamine, is a non-competitive antagonist with respect to serotonin and is competitively antagonized by harmine. On the other hand, the known product is a competitive antagonist with respect to serotonin; it is a non-competitive antagonist with respect to histamine and is not competitively antagonized by harmine.

In consequence, 1-(3'-benzofuryl)-4-benzylpiperazine and the known substance 1-acetyl-3-benzylpiperazinoindole are two analgesic compounds having entirely different modes of action.

Moreover, the compound in accordance with the invention has an advantage over morphine in that there is no attendant risk of addiction as is the case with morphine.

Thus, by virtue of these remarkable analgesic properties, the drug in accordance with the invention can be employed for the treatment of all ailments calling for the use of an analgesic which has a pain-relieving action equal to that of morphine.

The drug in accordance with the invention can be administered orally, for example in the form of tablets or capsules, in the form of suppositories for rectal administration or by intra-muscular injection in the form of a solution packed in ampoules.

When the drug in accordance with the invention is used orally, the dose to be taken each time is within the range of 10 to 20 mg of active substance, the daily dosage being preferably within the range of 30 to 100 mg of product.

In the case of rectal administration, the suppositories employed will preferably be dosed at 25 mg of active substance at a rate of 3 suppositories per day.

In the case of intra-muscular injection, the ampoules of injectable solution will preferably be dosed in a proportion of 20 mg of active substance, injections being performed at a rate of one to two per day.

A few examples of pharmaceutical forms of the drug in accordance with the invention are given hereinafter:

| | |
|---|---|
| Tablet: | |
| compound in accordance with the invention | 10 mg |
| polyvinylpyrrolidone, corn starch, talc, stearate | |
| q.s for one tablet of 150 mg. | |
| Capsule: | |
| compound in accordance with the invention | 10 mg |
| polyvinylpyrrolidone, corn starch, aerosil | |
| q.s. for one tablet of 150 mg. | |
| Suppository: | |
| compound in accordance with the invention | 25 mg |
| water for dispersing at 60° in semi-synthetic glycerides | |
| q.s. for one suppository of 2 g approx. | |
| Injectable solution: | |
| compound in accordance with the invention in the lyophilized state in a ampoule | 20 mg |
| ascorbic acid | 70 mg |
| water 1 ml, these two compounds being packed in a separate ampoule which is intended to be mixed at the time of use with the ampoule containing the compound in accordance with the invention. | |

What is claimed is:

1. An analgesic pharmaceutical composition containing an analgesically-effective amount of 1-(3'-benzofuryl)-4-benzylpiperazine and a pharmaceutically acceptable excipient.

2. Composition according to claim 1, in unit dosage form, wherein said analgesically effective amount is within the range of 10 to 20 mg.